United States Patent
Burrow

(10) Patent No.: US 7,388,509 B2
(45) Date of Patent: Jun. 17, 2008

(54) SYSTEM AND METHOD FOR DETECTING ELECTROLYSIS IN AN AUTOMOBILE SYSTEM

(75) Inventor: Patrick B. Burrow, Pipe Creek, TX (US)

(73) Assignee: International Lubricants, Inc., Seattle, WA (US)

( * ) Notice: Subject to any disclaimer, the term of this patent is extended or adjusted under 35 U.S.C. 154(b) by 145 days.

(21) Appl. No.: 11/238,818

(22) Filed: Sep. 28, 2005

(65) Prior Publication Data

US 2007/0069906 A1    Mar. 29, 2007

(51) Int. Cl.
*G08B 21/00* (2006.01)

(52) U.S. Cl. .............. 340/657; 340/438; 340/439; 340/459; 340/449; 340/450; 340/460; 214/400; 214/253; 429/12; 429/22; 429/23; 429/26

(58) Field of Classification Search .......... 340/657, 340/438, 439, 459, 449, 450, 460; 214/400, 214/253; 429/12, 22, 23, 26
See application file for complete search history.

(56) References Cited

U.S. PATENT DOCUMENTS

| | | | |
|---|---|---|---|
| 4,851,818 A | * | 7/1989 | Brown et al. .......... 340/603 |
| 5,656,771 A | * | 8/1997 | Beswick et al. .......... 73/118.1 |
| 5,888,385 A | | 3/1999 | Ische et al. |
| 6,187,197 B1 | | 2/2001 | Haddock |
| 6,540,966 B1 | | 4/2003 | Santilli |
| 6,545,603 B1 | | 4/2003 | Launay et al. |

FOREIGN PATENT DOCUMENTS

| | | |
|---|---|---|
| EP | 0 412 746 | 2/1991 |
| GB | 2 200 997 | 8/1988 |

OTHER PUBLICATIONS

McDarmont, Ralph; "Electrolysis Problems Continue to Mount"; Automotive Cooling Journal Jul. 2002; pp. 1-3.
Savasta, Bob; "Trouble Shooter"; MOTOR Sep. 2001; pp. 8-9.

* cited by examiner

*Primary Examiner*—Tai Nguyen
(74) *Attorney, Agent, or Firm*—Bryan G. Prau; Rader, Fishman & Grauer PLLC

(57) ABSTRACT

A system for detecting electrolysis in an automobile system includes a probe, a microcontroller electrically coupled to the probe, a power supply configured to supply power to the microcontroller, a ground lead, and an optical indicator operationally coupled to the microcontroller. According to one embodiment, the microcontroller is configured to read a voltage across the probe and the ground lead when the probe is inserted into a coolant fluid and the ground is coupled to a ground source, analyze the voltage, and illuminate the optical indicator in response to the voltage analysis.

5 Claims, 8 Drawing Sheets ature of the scaling. In areas with very poor water quality, trace amounts of metals may also be present, especially iron and lead.
SYSTEM AND METHOD FOR DETECTING ELECTROLYSIS IN AN AUTOMOBILE SYSTEM

FIELD

The present system and method relate to automobile fluid systems. More specifically, the present system and method provide a circuit for evaluating fluid purity by detecting electrolysis levels in an automotive cooling system.

BACKGROUND

Automotive cooling systems typically include one or more heat transferring fluid systems to maintain an internal combustion engine operating within a desired temperature range, thereby increasing efficiency. Many automotive cooling systems include a solution of antifreeze in water. The solution is pumped in a closed circuit that includes cooling jackets around the combustion chambers of the internal combustion engine where thermal energy is absorbed by the solution. The solution is then passed through a heat exchanger (radiator) where absorbed thermal energy is transferred out of the solution.

Antifreeze is a rather complex mixture of chemical components designed to perform a number of functions in the vehicle including protecting against overheating and freezing, protecting the many dissimilar metals within the cooling system from corrosion, acting as a buffer against acidic contamination, preventing foaming, preventing hard water scaling, reducing the consequences of oil fouling, and protecting diesel wet-sleeve liners from cavitation damage. All of these functions are important and demanding on an engine liquid coolant. Each of the above-mentioned functions must be specifically considered or, at some point, engine damage will occur. To obtain enhanced protection, engine liquid coolants often include a well-balanced additive package that may include up to 15 different inhibitors or more in addition to the commonly known components such as water, ethylene glycol, and dye. Most inhibitors are introduced as sodium or potassium salts and usually are specific in providing corrosion inhibition to one or two metals in the vehicle cooling system.

As antifreeze ages and undergoes hours of use in a vehicle's cooling system, it also accumulates many different types of contaminates. These include oil from leaking oil coolers and water pump lubricants, corrosion products in the form of metal ions and metal hydroxides (i.e., aluminum hydroxide can be produced through aluminum cylinder head corrosion), acids from blow-by gasses, and glycol degradation products such as glycolic, formic, oxalic, acetic acid. Other impurities may be present in the water used to dilute the antifreeze concentrate. These are ions, more commonly known as "minerals", and may include chlorides, sulfates, carbonates, and metal cations such as calcium and magnesium. Chlorides and sulfates are corrosive and calcium and magnesium cause scaling. In areas with very poor water quality, trace amounts of metals may also be present, especially iron and lead.

Due to the introduction of impurities with extended use of antifreeze in an automotive cooling system, the implementation of certain maintenance procedures is often required for extended coolant usage. The most common procedure is to remove and replace the engine coolant composition after a pre-established time period. In some instances, cooling system additives, which are alkaline and include corrosion inhibitors, are directly added to the coolant to enhance the coolant properties, decrease the corrosive effects, and postpone replacement of the coolant. However, detecting when replacement of the engine coolant or addition of an additive is needed has proven difficult absent the traditionally wasteful method of removing the coolant after a pre-determined period of time.

SUMMARY

An exemplary system for detecting electrolysis in an automotive cooling system includes a probe, a microcontroller electrically coupled to the probe, a power supply configured to supply power to the microcontroller, a ground lead, and an optical indicator operationally coupled to the microcontroller. According to one embodiment, the microcontroller is configured to read a voltage across the probe and the ground lead when the probe is inserted into a coolant fluid and the ground is coupled to a ground source, analyze the voltage, and illuminate the optical indicator in response to the voltage analysis.

An exemplary method for testing contamination levels in a coolant includes detecting stray currents in the coolant, and associating the detected stray current level to a purity level of the coolant.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

An exemplary system and method for detecting an electrolysis level in an automotive cooling system are disclosed herein. Specifically, the present exemplary system and method measures stray currents in an automobile cooling system to determine the purity and effectiveness of the coolants used in the tested automobile cooling system. Embodiments and examples of the present exemplary systems and methods will be described in detail below.

Unless otherwise indicated, all numbers expressing quantities, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

As used herein, the term "electrolysis" is meant to be understood broadly both here and in the appended claims as including any conduction of electricity through a substance with an accompanying chemical reaction.

In the following description, for purposes of explanation, numerous specific details are set forth in order to provide a thorough understanding of the present system and method for detecting an electrolysis level in a cooling system of an automobile. It will be apparent, however, to one skilled in the art, that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
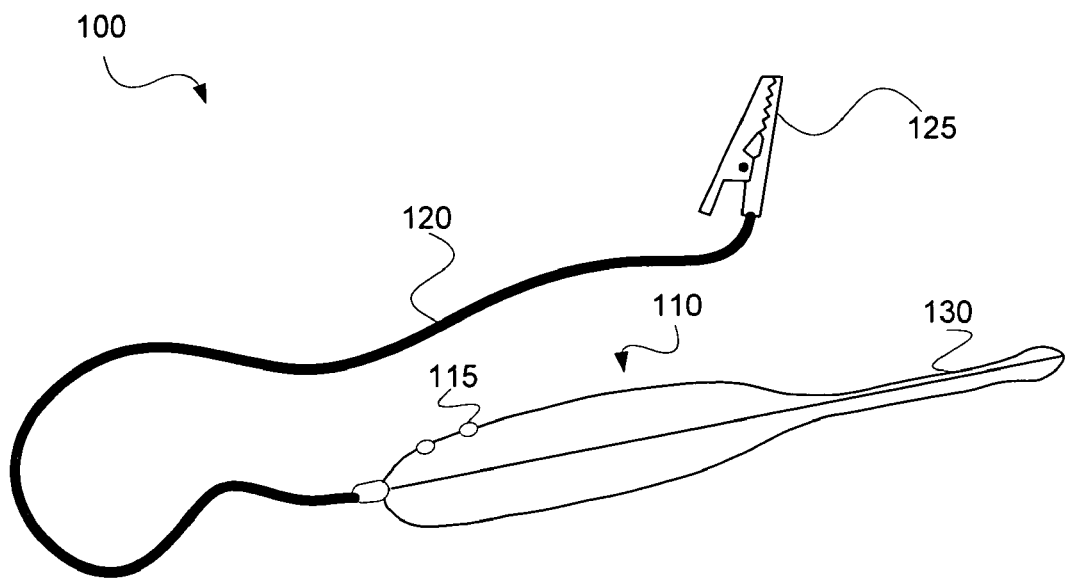
FIG. 1 is a side view illustrating an electrolysis indicator, according to one exemplary embodiment.
Figure 2:
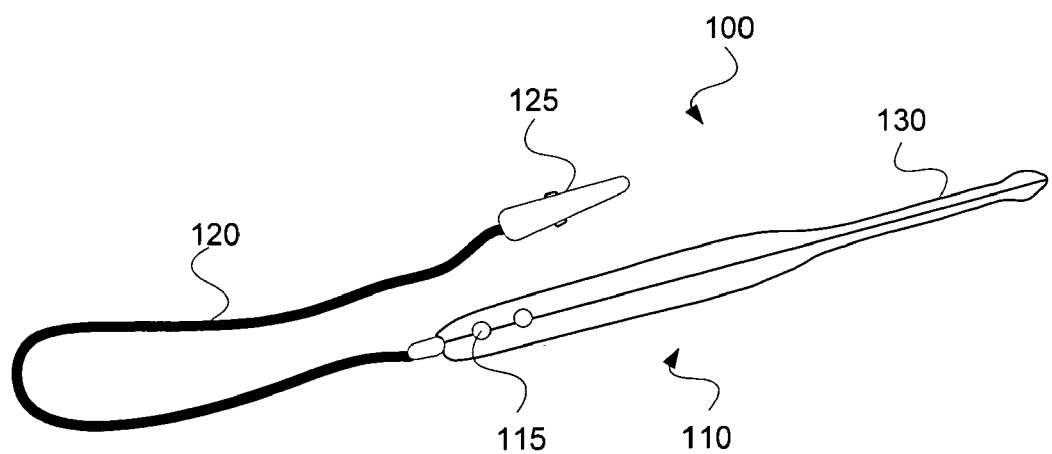
FIG. 2 is a top view illustrating an electrolysis indicator, according to one exemplary embodiment.

FIGS. 1 through 4b illustrate exemplary components of an electrolysis detection system (100), according to a number of exemplary embodiments. As illustrated in FIGS. 1 and 2, the exemplary electrolysis detection system (100) includes a body (110) having a protruding probe body (130) and an optical indicator (115) formed therein. Additionally, a ground wire (120) with a ground connector (125) is coupled to one end of the body (110), according to one exemplary embodiment. Further details of the exemplary components will be described in further detail below.

As mentioned, the exemplary electrolysis detection system (100) includes a body (110) having a protruding probe body (130) and an optical indicator (115) formed therein. According to the exemplary embodiment illustrated in FIGS. 1 and 2, the body (110) of the electrolysis detection system (100) is configured to house and structurally support a number of electronic components while testing the electrolysis levels in a vehicle coolant. Consequently, the body (110) of the electrolysis detection system (100) may be formed out of any number of materials including, but in no way limited to, plastics, thermoplastics, composites, metals, and combinations thereof. Similarly, the exemplary body (110) portion of the electrolysis detection system (100) may be formed according to any number of material formation methods including, but in no way limited to, injection molding.

According to the exemplary embodiment illustrated in FIGS. 1 and 2, the probe body (130) protrudes from the body (110), facilitating insertion of the probe into the fluid of a desired cooling system. As shown, the probe body (130) includes a cylindrical protruding member intimately coupled to the main body (110).

Additionally, one or more optical indicators (115) are formed into the main body (110) of the exemplary electrolysis indicator (100), according to the exemplary embodiment. While the present exemplary electrolysis indicator (100) will be described herein in the context of a number of light emitting diodes (LEDs) having varying colors to indicate varying qualities of the tested cooling fluid, any number or style of optical indicators (115) may be employed by the present exemplary electrolysis detection system (100) including, but in no way limited to, organic light emitting devices (OLEDs), light emitting polymer (LEP) displays, liquid crystal displays (LCDs), and the like. According to the present exemplary embodiment illustrated in FIGS. 1 and 2, two optical indicators (115) may be used to optically display the purity of the coolant being tested. The use of more than one optical indicators (115) exhibiting differing illumination colors is configured to ease the assessment of the usability and purity of the coolant being tested, according to one exemplary embodiment. However, the optical indicators (115) may be configured to provide a quantitative evaluation of the amount of electrolysis taking place in the tested cooling system, according to one exemplary embodiment, described in further detail below.

Coupled to the main body (110) is a ground wire (120) and a ground connector (125). According to one exemplary embodiment, illustrated in FIGS. 1 and 2, the ground wire (120) is coupled to the main body (110) opposite the probe body (130). As illustrated, the ground wire (120) provides a conductive medium for generating a ground contact for the internal electronics of the exemplary electrolysis detection system (100). The ground wire (120) may assume any number of lengths sufficient to reach a grounding surface, while allowing the probe body (130) of the electrolysis detection system (100) to be inserted into a fluid being tested. According to the exemplary embodiment illustrated in FIGS. 1 and 2, the ground connector (125) includes an alligator clip configured to be coupled to a negative terminal on an automotive battery, thereby providing the ground contact for the internal electronics. Alternatively, any number of conductive couplers may be formed on the end of the ground wire (120) to provide a ground contact for the present exemplary electrolysis detection system (100).

Figure 3:
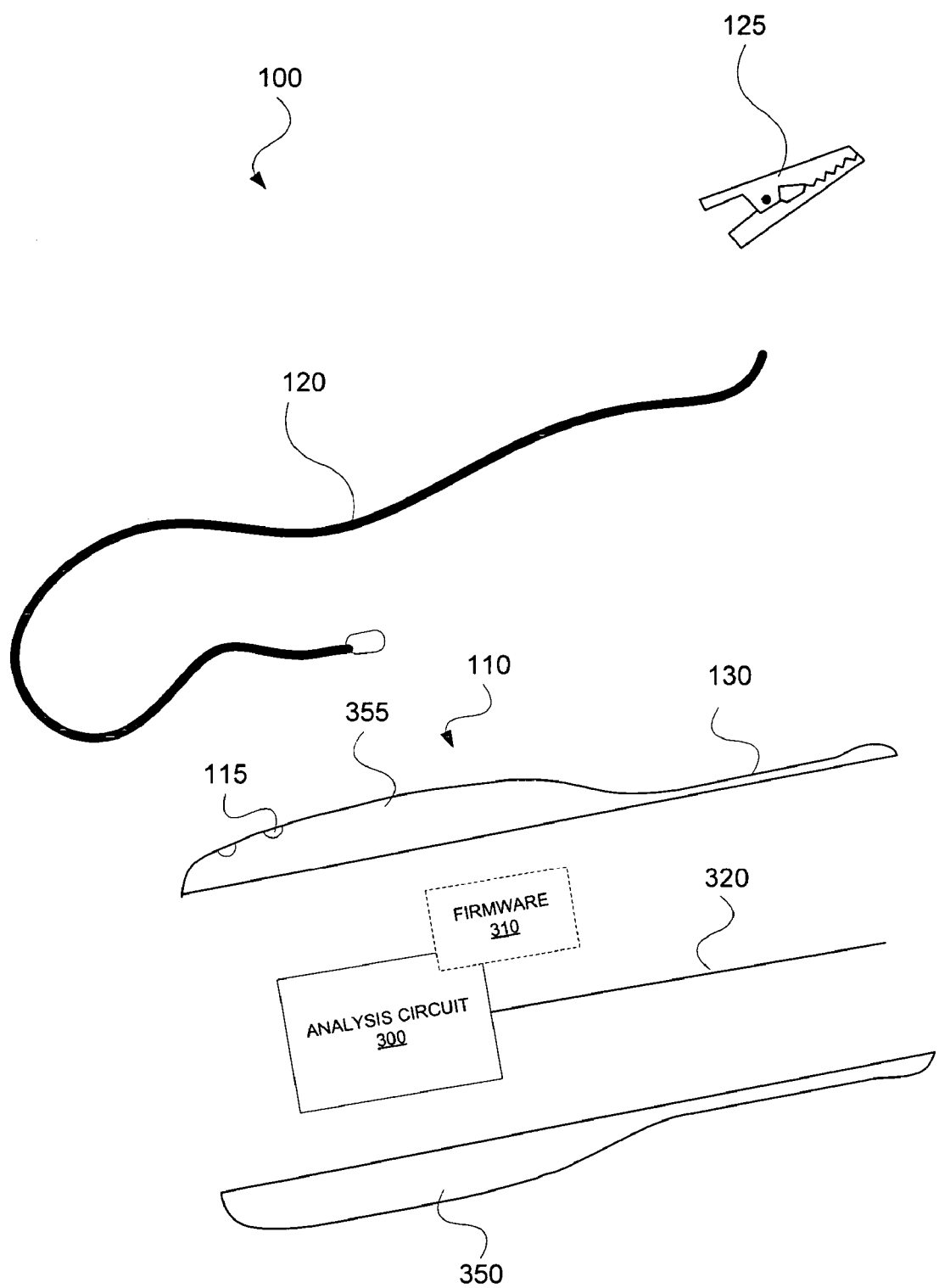
FIG. 3 is an exploded side view illustrating the components of an electrolysis indicator, according to one exemplary embodiment.

FIG. 3 further illustrates the components of the exemplary electrolysis detection system (100), according to one exemplary embodiment. As illustrated in FIG. 3, the main body (110) of the electrolysis detection system (100) may be separated into a bottom body member (350) and a top body member (355). Alternatively, the main body (110) may be formed of a plurality of side members. As illustrated in FIG. 3, the bottom body member (350) and the top body member (355) are coupled around an analysis circuit (300) electrically coupled to a probe (320). Additionally, as illustrated in FIG. 3, the analysis circuit is configured to perform a number of detection and evaluation operations referred to herein as firmware (310).

According to one exemplary embodiment, the probe (320) that is electrically coupled to the analysis circuit (300) may be any number of conductive materials configured to translate a detectable electric signal including, but in no way limited to metals such as gold, silver, and copper.

Figure 4A:
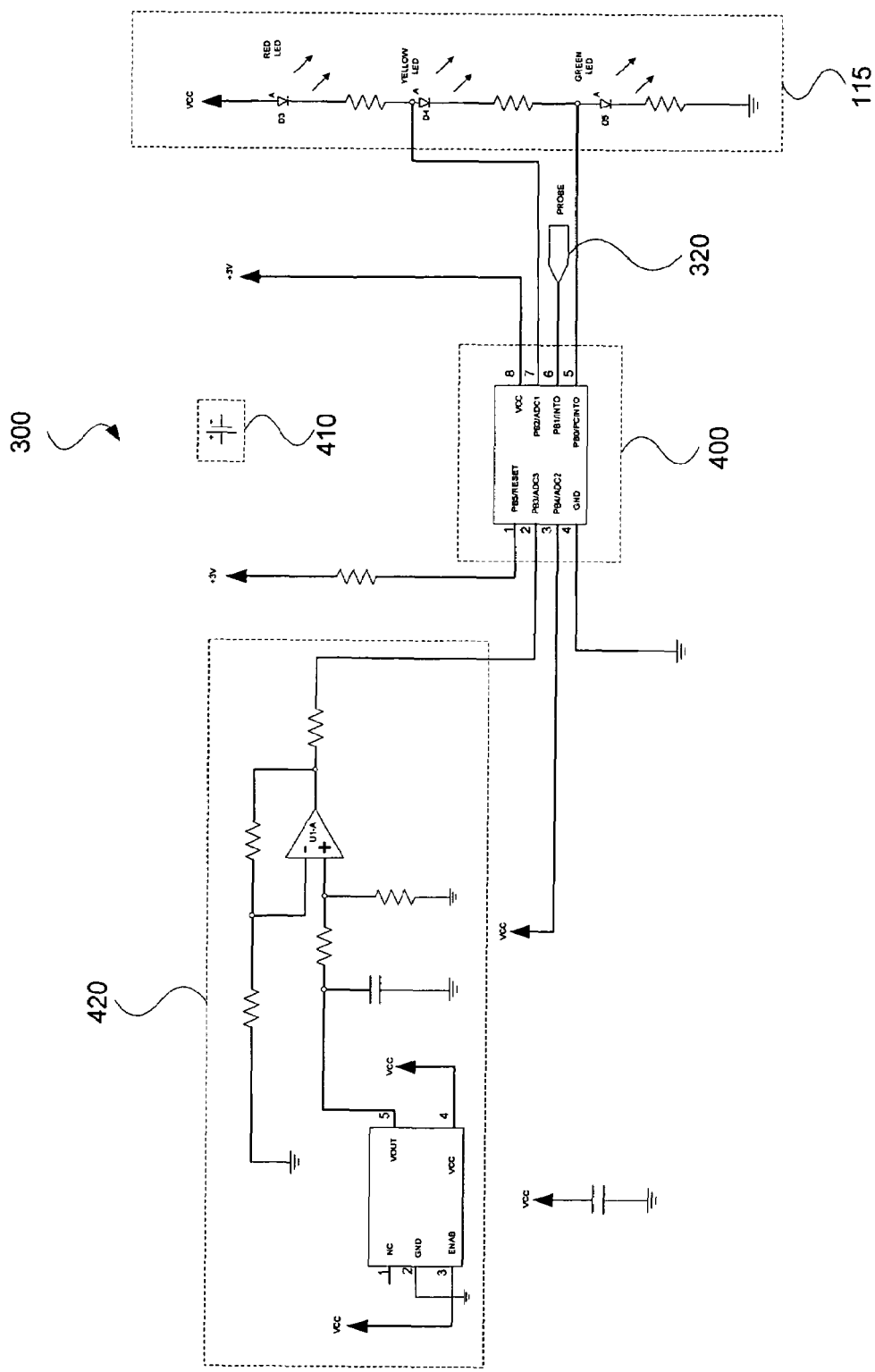
FIGS. 4a and 4b are circuit diagrams illustrating the components of various analysis circuits, according to various exemplary embodiments.

FIG. 4a illustrates an exemplary circuit diagram representing the analysis circuit (300), according to one exemplary embodiment. While the exemplary circuit diagram illustrates a number of logical circuit elements configured to work together to perform the present firmware based analysis, the analysis circuit is in no way limited to the illustrated embodiment. Rather, the logical analysis circuit (300) may assume any number of configurations, or alternatively, may be replaced by any number of stand alone processors programmed to perform the present firmware (310) functions.

According to the exemplary embodiment illustrated in FIG. 4a, the logical analysis circuit (300) includes, but is in no way limited to, a probe connection (320), one or more optical indicators (115), a power supply (410), and a differential operational amplifier (420) communicatively coupled to a microcontroller (400). Details of the exemplary logical analysis circuit (300) will be provided below.

As shown, the exemplary analysis circuit (300) includes a microcontroller (400) communicatively coupled to a number of other components. According to one exemplary embodiment, the microcontroller (400) of the exemplary analysis circuit (300) may include, but is in no way limited to, a central processing unit (CPU), a microprocessor, or any other device made from miniaturized transistors and other circuit elements on one or more semiconductor integrated circuits (IC). According to the exemplary embodiment illustrated in FIG. 4a, the microcontroller (400) is configured to receive stray current inputs from the probe (320) and, based on the stray currents, perform the firmware (310; FIG. 3) functions to evaluate the contamination of an antifreeze fluid.

According to one exemplary embodiment, after the main processor receives a stray current input from the probe (320), the differential operational amplifier (420) conditions the signal for determination by the microcontroller (400). FIG. 4a also illustrates the power supply (410) providing power to the analysis circuit (300). According to one exemplary embodiment, the power supply (410) includes, but is in no way limited to, one or more batteries such as two 1.5 volt AAA batteries. According to the exemplary embodiment illustrated in FIG. 4a, the exemplary power supply (410) provides power to the microcontroller (400), which then feeds power to the differential operational amplifier (420).

As illustrated in FIG. 4a, the exemplary analysis circuit (300) includes an optical indicator (115) in the form of a red LED, a yellow LED, and a green LED. According to this exemplary embodiment, the analysis circuit (300) is configured to illuminate the green LED when detected voltage levels are indicative of good coolant purity, illuminate the yellow LED when the detected voltage levels indicate a coolant purity that could use an additive or is near unacceptable contamination levels, and illuminate the red LED when the detected voltage levels are indicative of unacceptable contamination levels.

Figure 4B:
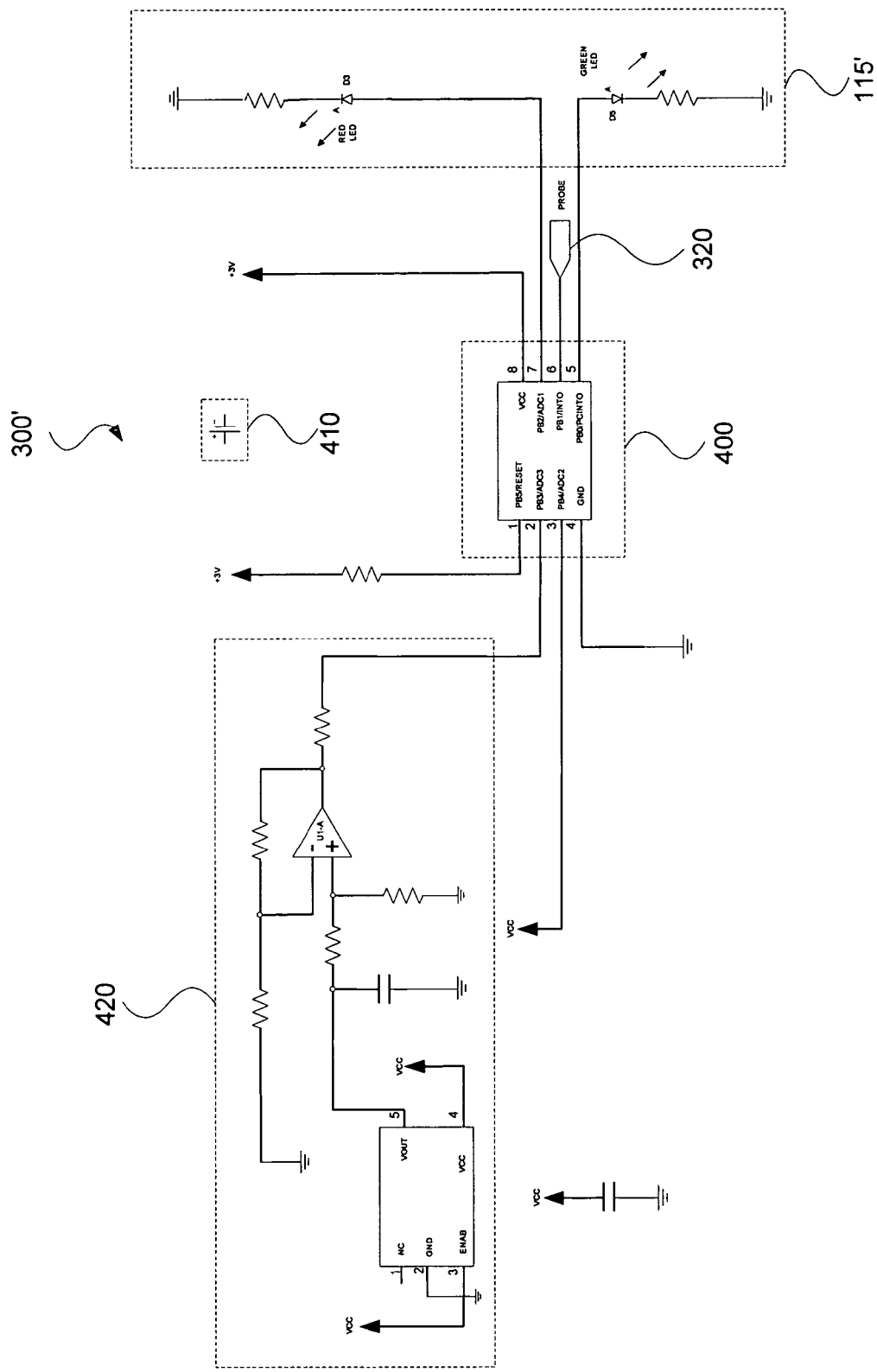

FIG. 4b illustrates an alternative exemplary analysis circuit (300'), according to one exemplary embodiment. As illustrated in FIG. 4b, the optical indicator (115') is reduced to a pair of LEDs. According to one exemplary embodiment, the optical indicator (115') includes a red LED and a green LED. According to this exemplary embodiment, a threshold detection voltage is established as a baseline for the quality of the coolant being tested. More specifically, if the detected stray voltage level is below a pre-determined voltage, the coolant is considered "good" and the green LED is illuminated. If, however, the detected stray current level is above the pre-determined voltage, the coolant is considered "bad" and the red LED is illuminated. According to this exemplary embodiment, the possible indecisiveness of the yellow LED illustrated in FIG. 4a is eliminated. Further details of the operation of the present electrolysis detection system (100; FIG. 1) and the performance of the firmware (310; FIG. 3) by the exemplary analysis circuits (300, 300') will be described in detail below.

Exemplary Implementation and Operation

Figure 5:
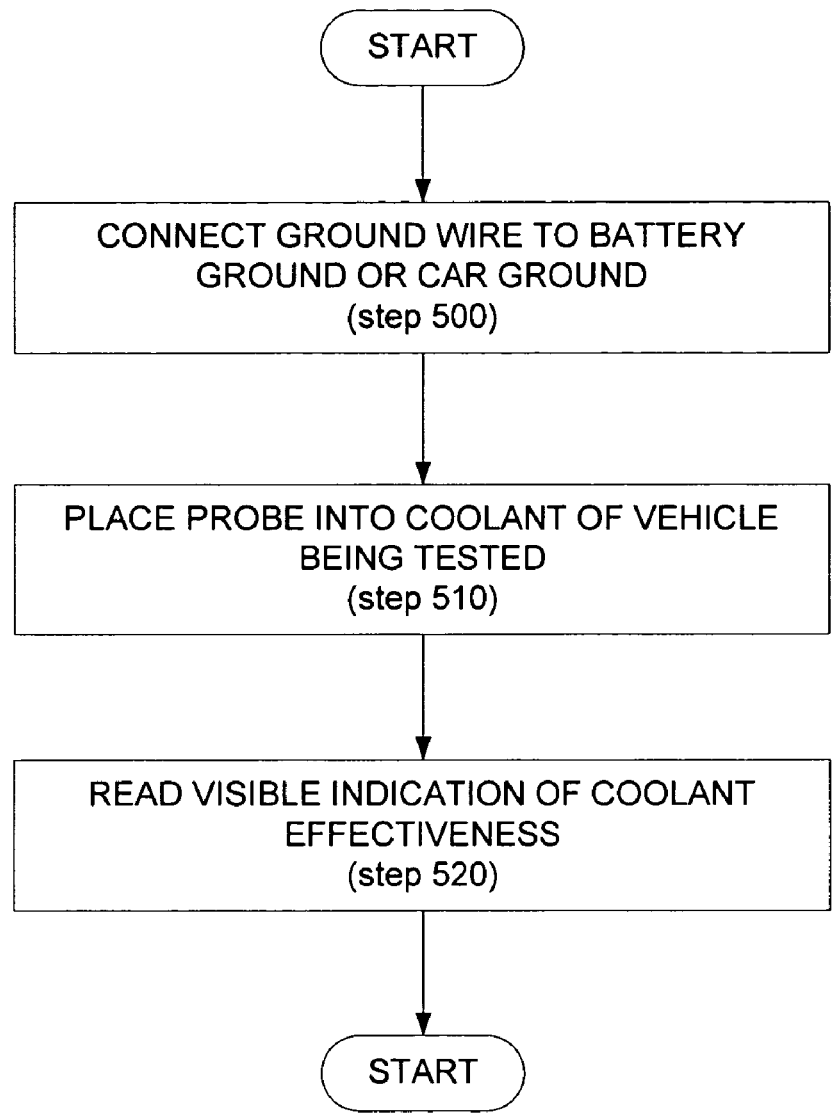
FIG. 5 is a flowchart illustrating a method for testing the electrolysis level in an automotive coolant, according to one exemplary embodiment.

FIGS. 5 through 7b illustrate exemplary methods for operating the above-mentioned electrolysis detection system (100; FIG. 1), according to one exemplary embodiment. As illustrated in FIG. 5, the exemplary electrolysis detection system (100; FIG. 1) may be connected to an automobile cooling system in order to test the contamination of the antifreeze or other coolant by first connecting the ground wire (120; FIG. 1) of the electrolysis detection system to a battery ground terminal or a car ground (step 500) such as an engine block. Secondly, the probe body of the electrolysis detection system (100; FIG. 1) is placed into the coolant of the vehicle being tested (step 510). With the probe body of the electrolysis detection system properly inserted into the coolant of the vehicle being tested, the stray currents present in the coolant may then be detected and used to produce a visible indication of coolant condition or contamination level (step 520).

Figure 6:
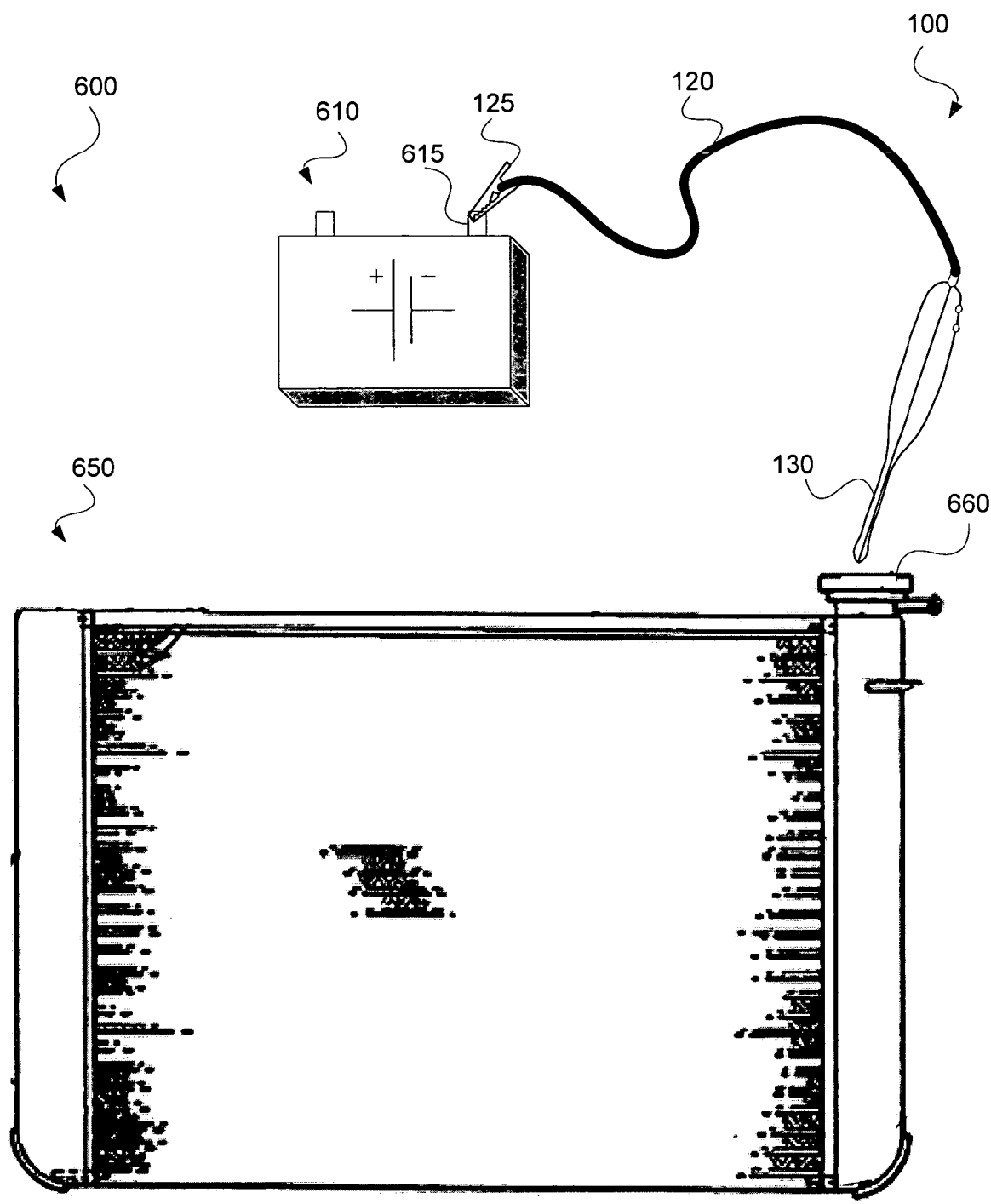
FIG. 6 is a perspective view of the electrolysis indicator of FIG. 1 coupled to an automobile cooling system, according to one exemplary embodiment.

FIG. 6 illustrates the present electrolysis detection system (100) coupled to an automotive cooling system in a testing configuration (600), according to one exemplary embodiment. As illustrated in FIG. 6, the electrolysis detection system (100) is first coupled to a negative terminal (615) of an automobile battery (610) to provide a ground path for the system (step 500; FIG. 5). As shown, the ground connector (125) in the form of a gator clip or other coupling device may be coupled to the negative terminal (615). Alternatively, the ground path for the electrolysis detection system (100) may be established by coupling the ground connector to an engine block of the automobile, or another grounded surface.

With the electrolysis detection system properly grounded (step 500; FIG. 5), the probe body (130) of the electrolysis detection system (100) may be placed into the coolant of the vehicle being tested (step 510; FIG. 5). As illustrated in FIG. 6, the radiator cap of a vehicle radiator (650) may be removed, after sufficient cooling of the system, and the probe body (130) inserted into the radiator inlet (660). During insertion of the probe body (130) into the radiator (650), false readings are avoided if the probe body (130) contacts the radiator core by shielding the tip of the probe body.

According to one exemplary embodiment, once the illustrated testing configuration (600) is established, a number of test results may be obtained under differing operating conditions, to thoroughly evaluate the condition or contamination level of the coolant in the radiator (650) and the remainder of the coolant system. According to one exemplary embodiment, a base (first) test may be preformed with the vehicle not running. This allows for an initial evaluation of the stray currents without vehicle accessories contributing to the readings. Once the base test is performed, the vehicle may be started, again with all vehicle accessories turned off, and another reading taken. With the second reading taken, each vehicle accessory, such as radios, air conditioning, lights, and the like, may be turned on, one by one, watching for voltage changes. Changes in the stray voltages detected by the electrolysis detection system (100) after the activation of a vehicle accessory may indicate which accessory may be causing a voltage leakage into the cooling system.

Figure 7A:
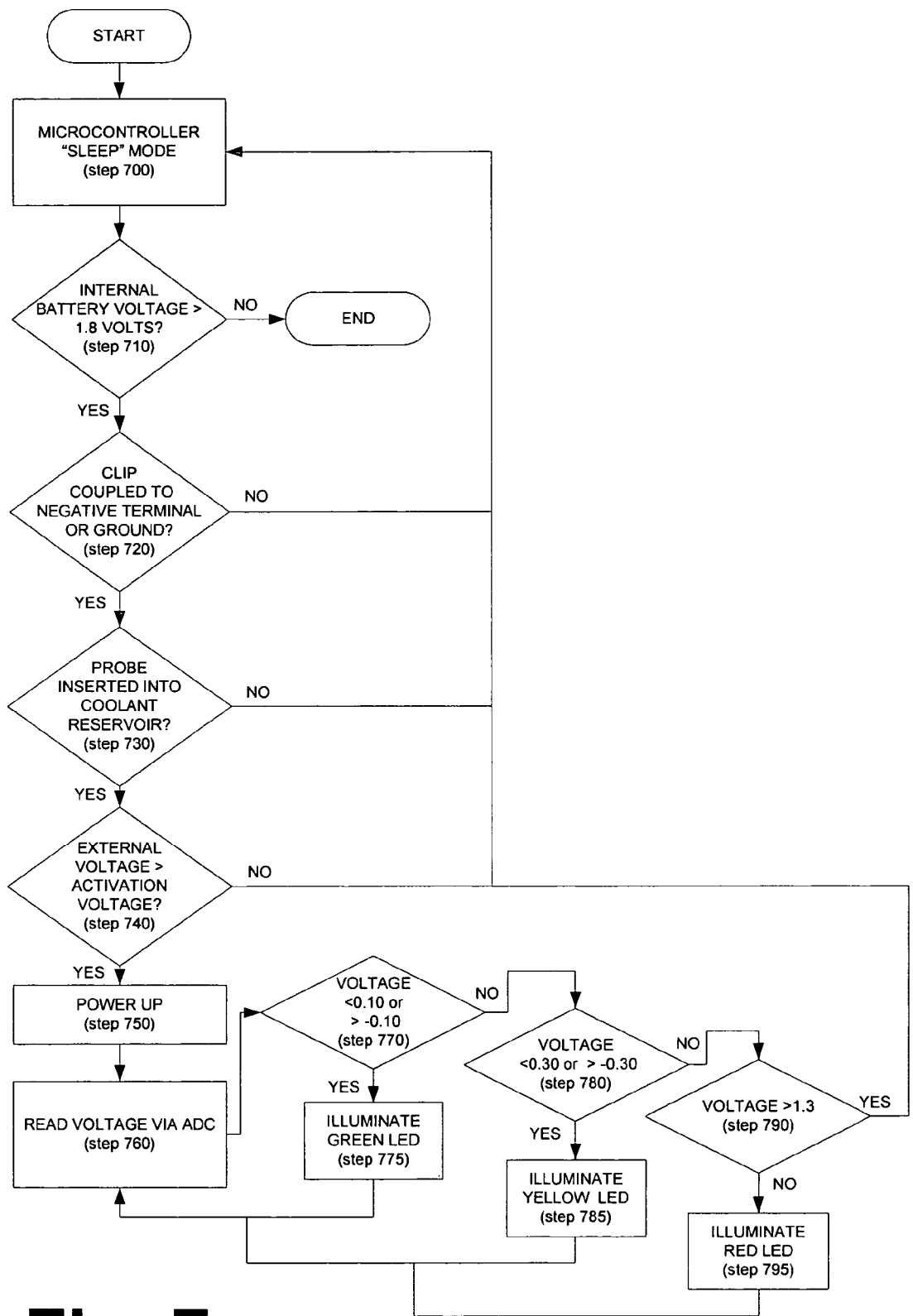
FIGS. 7a and 7b are flowcharts illustrating processes that occur within the electrolysis indicator during operation, according to exemplary embodiments.
Figure 7B:
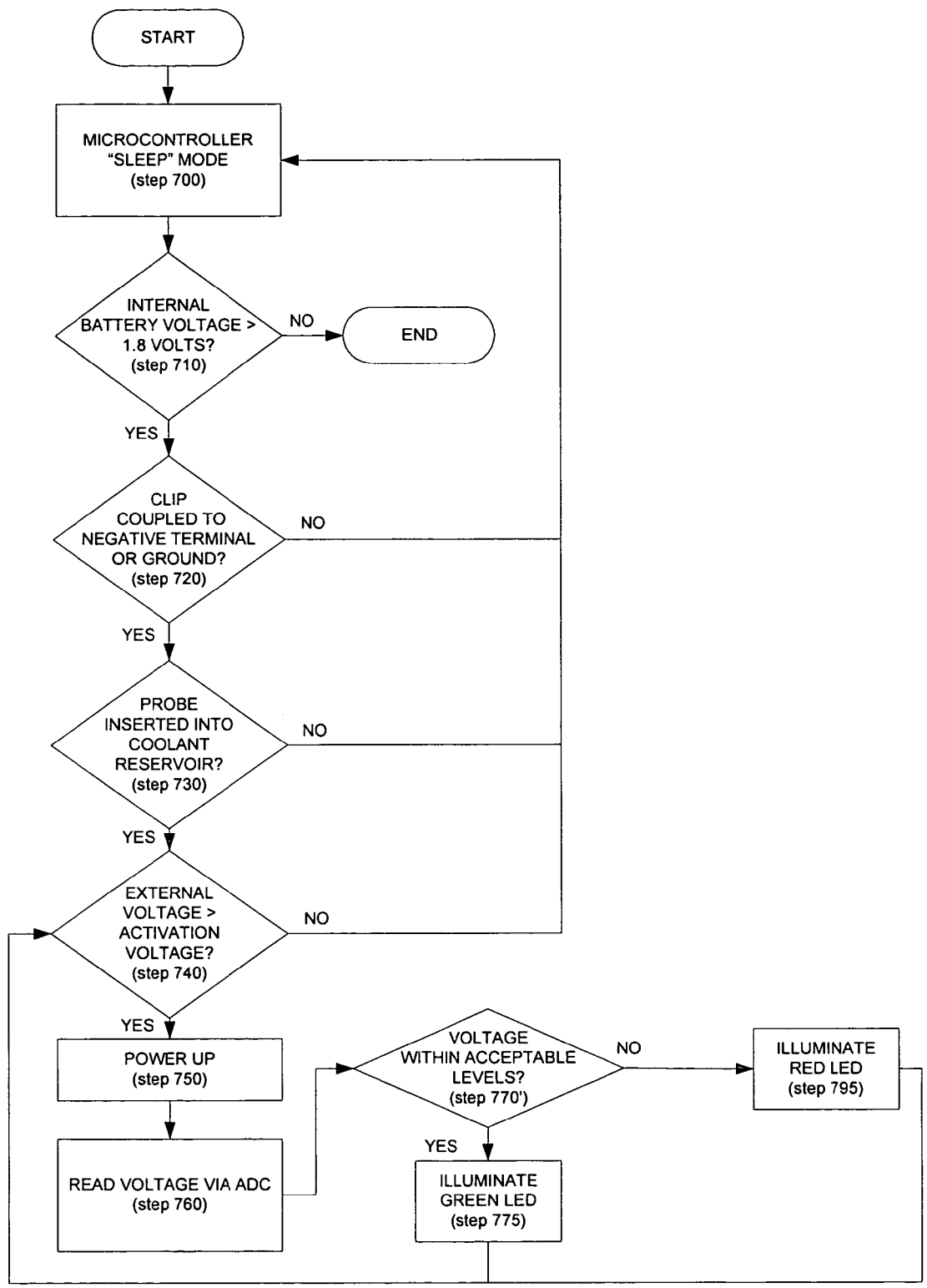

During the various tests of an identified cooling system, the visible indications of the coolant effectiveness, measured by the amount of stray currents detected in the system (step 520; FIG. 5), are performed by the analysis circuit (300; FIG. 4) executing the firmware (310; FIG. 3) operations. FIGS. 7a and 7b illustrate exemplary methods of performing the firmware operations during testing of a desired coolant, according to one exemplary embodiment. The method of FIG. 7a will be described below, with reference to the analysis circuit components illustrated in FIG. 4a and the method of FIG. 7b will be described with reference to the analysis circuit components illustrated in FIG. 4b.

As illustrated in FIG. 7a, prior to insertion of the probe (320) into an identified coolant, no voltage is measured across the analysis circuit (300) and the microcontroller (400) remains in a state of dormancy referred to herein as the sleep mode (step 700). When in the sleep mode, the analysis circuit (300) continually checks the internal battery voltage to assure that it is above a threshold level recommended for operation (step 710). According to one exemplary embodiment, the power for the analysis circuit (300) is provided by a power supply (410) in the form of two 1.5 volt AAA batteries. According to this exemplary embodiment, the microcontroller (400) is powered directly from the two AAA batteries, which then supply power to the remaining components of the analysis circuit (300). When in sleep mode, the analysis circuit may have an electronic current draw from the power supply of approximately 0.10 uAmps. According to this exemplary embodiment, if the internal battery voltage drops below a threshold level of approximately 1.8 volts (NO, step 710), battery replacement is recommended and operation of the system ends.

However, if the internal battery voltage is above the determined threshold (YES, step 710), the analysis circuit (300) determines whether the ground connector (125; FIG. 1) is coupled to a negative battery terminal or ground (step 720) and whether the probe (320) is inserted into a coolant reservoir (step 730). If either the ground connector is not coupled to a negative battery terminal or ground (NO, step 720), or the probe is not inserted into a coolant reservoir (NO, step 730), the microcontroller continues in its sleep mode (step 700). This occurs due to the inability to detect an external voltage when neither condition is met.

If, however, the ground connector is coupled to a negative battery terminal or ground (YES, step 720) and the probe is inserted into a coolant reservoir (YES, step 730), the exemplary analysis circuit (300) determines if the external voltage detected is greater than a pre-determined activation voltage (step 740). More particularly, when the ground connector is appropriately connected and the probe is inserted into a coolant reservoir, a voltage is read across the probe (320) and the ground connector. If the external voltage does not reach a threshold voltage (NO, step 740), the analysis circuit (300) remains in a dormant sleep state (step 700). If, however, the external voltage does meet or exceed a threshold voltage (YES, step 740) the microcontroller (400) is configured to power up (step 750). According to one exemplary embodiment, the threshold voltage is approximately 0.3 volts read across the probe (320) and the ground connector.

Once powered up, the microcontroller (400) is continuously reading and analyzing the voltage across the probe (320) end and the ground connector using an analog to digital converter (ADC) (step 760). Prior to reading this voltage, the firmware turns on the power supply (410) voltage to an internal resistance which is placed in a series connection to a probe input pin (6) of the microcontroller (400). The probe input pin (6) is then said to be in a "pull up state." This internal resistance placed on the microcontroller (400) pin (6) and the voltage level across the probe (320) end and the ground connector create a voltage divider which the analysis circuit (300) reads.

As mentioned previously, the present exemplary embodiment is configured to present a user with an optical signal in the form of one of a plurality of colored LED displays. However, the direct readout of the ADC may also be displayed to a user by way of any number of the previously mentioned displays. Continuing with FIGS. 4a and 7a, once the voltage is conditioned by the differential operational amplifier (420) and converted via the ADC (step 760), it is analyzed by the microcontroller (400). Specifically, the output of the ADC is compared via firmware to a low threshold voltage and a high threshold voltage. First, the microcontroller determines if the amount of stray currents correspond to an appropriate voltage range indicating proper antifreeze purity (step 770). According to the illustrated embodiment, if the detected voltage is between approximately −0.10 and 0.10 volts (YES, step 770), the amount of stray currents are appropriate and indicate proper fluid purity. Consequently, a green LED, indicating proper fluid purity, may be illuminated (step 775) and the analysis circuit (300) continues to read the detected voltage (step 760). According to the exemplary analysis circuit (300) illustrated in FIG. 4a, the illumination of a green LED (D5) may include the microcontroller (400) turning on the battery voltage to pin 5 and pin 7 of the microcontroller, which turns on light emitting diode D5 and turns off light emitting diodes D3 and D4.

If the detected voltage is not below the lower threshold value (NO, step 770), the microprocessor (400) continues by determining if the detected voltage is between approximately 0.30 or −0.30 volts (step 780). If the voltage is between approximately 0.30 or −0.30 volts (YES, step 780), a yellow LED (D4) may be illuminated (step 785) to indicate that the stray current levels are indicative of a contamination level that may be of some concern, and may warrant an additive or replacement of the coolant fluid.

If, however, the detected voltage is not between approximately 0.30 or −0.30 volts (NO, step 780), the voltage exceeds an upper threshold, such as approximately 0.30 volts, indicating excessive contamination due to electrolysis in the cooling system. When this high voltage is detected, the analysis circuit (300 determines whether the high value is due to high contaminant levels or improper use. Consequently, the analysis circuit (300) determines whether the detected voltage exceeds approximately one half of the power supply voltage, or approximately 1.3 volts (step 790). If the detected value exceeds approximately one half of the power supply voltage (YES, step 790), the firmware determines that the voltage across the probe (320) and the ground connector (125; FIG. 1) has been removed and the microcontroller (400) powers down and enters a microcontroller sleep mode (step 700). If, however, the detected high voltage is less than approximately half the power supply voltage, or 1.3 volts (NO, step 790), the firmware determines that the analysis circuit is still being used properly, and the high voltage is due to high contamination levels in the coolant, caused by electrolysis of the coolant system. Consequently, a red LED (D3) may be illuminated (step 795) and the analysis circuit (300) continues operation (step 760).

In contrast to the exemplary method illustrated in FIG. 7a, the exemplary method of FIG. 7b illustrates operation of the alternative analysis circuit (300') illustrated in FIG. 4b. As illustrated in FIG. 7b, the initial operation steps are very similar to those described above with reference to FIG. 7a. Specifically, the alternative analysis circuit (300') also operates in sleep mode (step 700) until the internal battery voltage is greater than approximately 1.8 volts (YES, step 710), the clip is coupled to a negative terminal or ground (YES, step 720), the probe is inserted into a coolant reservoir (YES, step 730), and the detected voltage is greater than an activation voltage (YES, step 740).

Once the above-mentioned conditions are satisfied, the alternative analysis circuit (300') powers up (step 750) and a voltage across the probe (320) end and the ground connector using an analog to digital converter (ADC) (step 760). According to the exemplary method illustrated in FIG. 7b, the microprocessor (400) first determines whether the detected voltage is within acceptable voltage levels indicative of acceptable coolant purity (step 770'). According to this exemplary embodiment, the acceptable voltage level may be programmed into the microprocessor (400) as deemed appropriate by the manufacturer or an automotive technician. If the detected voltage level is within the predetermined acceptable levels (YES, step 770'), a green LED is illuminated (step 775), optically indicating to a user that the coolant is acceptable. If, however, the detected voltage is not within the predetermined acceptable levels (NO, step 770'), the analysis circuit (300') illuminates a red LED (D3) may be illuminated (step 795) and the analysis circuit (300') continues operation (step 740). According to one exemplary embodiment, the predetermined acceptable voltage limits that result in the illumination of a green optical indicator rather than a red optical indicator may be approximately 0.3v. That is, if the detected voltage is above approximately 0.3v, a red LED or other optical indicator is illuminated, indicating an unacceptable level of contamination in the coolant.

Alternative Embodiment

While the present exemplary electrolysis detection system (100) has been described in the context of a hand held quality detection tool configured for use by an auto mechanic or an automobile owner, the present electrolysis detection system may be a hardwired component forming an integral component of an automobile sensor system. According to this exemplary embodiment, a probe will be continually present in an automobile cooling system, detecting stray currents and transmitting the currents to a microcontroller or other CPU of the automobile. When unsafe levels of stray currents are detected that may indicate unsafe levels of electrolysis in the coolant system, an audible and/or visible alarm may be presented to the vehicle operator, notifying them of a need to "check engine," or "change coolant." Alternatively, the results of the continual current monitoring may be stored in a data storage device, such as a read only memory (ROM) or a random access memory (RAM) unit, to be accessed and analyzed by an authorized mechanic during oil changes or other regularly scheduled tune-ups.

In conclusion, the present exemplary system and method for detecting an electrolysis level in a cooling system of an automobile is configured to evaluate the purity and effectiveness of the coolant fluid in a system, based on an amount of stray currents. According to one exemplary embodiment, the electrolysis detection system aids in the diagnosis and correction of stray electric currents within an automobiles coolant system. The EI utilizes a microcontroller, several analog components, and three light emitting diodes to process information and indicate to the user the range of stray current detected, thereby simplifying analysis of the detected stray currents.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:

1. An apparatus comprising:
   a probe;
   a microcontroller electrically coupled to said probe;
   a power supply configured to supply power to said microcontroller;
   a ground lead; and
   an optical indicator operationally coupled to said microcontroller;
   wherein said microcontroller is configured to read a voltage across said probe and said ground lead when said probe is inserted into a coolant and said ground lead is coupled to a around source, analyze said voltage, and activate said optical indicator in response to said voltage analysis;
   wherein said optical indicator includes a plurality of light emitting diodes (LEDS), each of said plurality of light emitting diodes being configured to illuminate a different colored light, each of said colored lights indicating a varying coolant purity; and
   wherein said microcontroller is configured to associate said voltage to a coolant purity and illuminate one of said LEDs in response to said purity association.

2. The apparatus of claim 1, wherein said plurality of LEDs comprises:
   a green LED associated with acceptable voltages; and
   a red LED associated with unacceptable voltage levels.

3. The apparatus of claim 2, wherein said acceptable voltage comprises a detected voltage less than approximately 0.3 volts.

4. An automobile coolant testing apparatus comprising:
   a probe;
   a ground lead;
   an optical indicator;
   a microcontroller electrically coupled to said probe and said ground lead, and operationally coupled to said optical indicator, wherein said microcontroller is configured to read a voltage across said probe and said ground lead when said probe is inserted into a coolant and said ground lead is coupled to a ground source, analyze said voltage, and illuminate said optical indicator in response to said voltage analysis;
   a power supply configured to supply power to said microcontroller;
   a differential operational amplifier coupled to said microcontroller, wherein said differential operational amplifier is configured to condition said read voltage;
   an analog to digital converter (ADC) disposed between said differential operational amplifier and said microcontroller, said ADC being configured to convert said read voltage to a digital value;
   wherein said optical indicator comprises a plurality of light emitting diodes (LEDs), each of said plurality of light emitting diodes being configured to illuminate a different colored light, each of said colored lights indicating a varying coolant purity; and
   wherein said microcontroller is configured to associate said voltage to a coolant purity and illuminate one of said LEDs in response to said purity association.

5. The automobile coolant testing apparatus of claim 4, wherein said plurality of LEDs comprise:
   a green LED associated with acceptable voltages; and
   a red LED associated with unacceptable voltage levels.

* * * * *

UNITED STATES PATENT AND TRADEMARK OFFICE
CERTIFICATE OF CORRECTION

| | | |
|---|---|---|
| PATENT NO. | : 7,388,509 B2 | Page 1 of 1 |
| APPLICATION NO. | : 11/238818 | |
| DATED | : June 17, 2008 | |
| INVENTOR(S) | : Patrick B. Burrow | |

It is certified that error appears in the above-identified patent and that said Letters Patent is hereby corrected as shown below:

Column 10, Line 10, Claim 1, change "lead is coupled to a around source" to --lead is coupled to a ground source--

Signed and Sealed this

Twelfth Day of August, 2008

JON W. DUDAS
*Director of the United States Patent and Trademark Office*